United States Patent [19]

Wood et al.

[11] 4,436,813

[45] Mar. 13, 1984

[54] IMMOBILIZED MICROBIAL CELL COMPOSITION FOR MAKING L-ASPARTIC ACID

[75] Inventors: Louis L. Wood, Rockville; Gary J. Calton, Elkridge, both of Md.

[73] Assignee: Purification Engineering, Inc., Columbia, Md.

[21] Appl. No.: 358,784

[22] Filed: Mar. 16, 1982

[51] Int. Cl.³ .................... C12P 13/20; C12N 11/12; C12N 11/08; C12N 11/04
[52] U.S. Cl. .................................. 435/109; 435/176; 435/179; 435/180; 435/182
[58] Field of Search ............... 435/109, 174, 178, 179, 435/182, 180

[56] References Cited

U.S. PATENT DOCUMENTS

| | | | |
|---|---|---|---|
| 3,791,926 | 2/1974 | Chibata et al. | 435/109 |
| 3,860,490 | 1/1975 | Guttag | 435/182 |
| 4,138,292 | 2/1979 | Chibata et al. | 435/182 |
| 4,237,229 | 12/1980 | Hartdegan et al. | 435/182 |

OTHER PUBLICATIONS

Fusee et al., Immobilization of *Eccherichiz coli*, Cells Containing Aspartase Activity with Polyurethane and Its Application for L-Aspartic Acid Production, Applied and Environmental Microbiology, vol. 42, No. 4, 1981, (pp. 672–676).

Hustad et al., Immobilization of Beta-Galactosidage on an Insoluble Carrier with a Polyisocyanate Polymer.I Preparation and Properties, J. Da. Sci., vol. 56, No. 9, 1973, (pp. 1111–1177).

*Primary Examiner*—David M. Naff
*Attorney, Agent, or Firm*—Cushman, Darby & Cushman

[57] ABSTRACT

Microbial cells having L-aspartase activity are immobilized for producing L-aspartic acid. The cells are immobilized by mixing the cells with a curable prepolymer material and curing the prepolymer material to form a crosslinked polymer. Suitable prepolymer materials are polyazetidine prepolymers, carboxymethyl cellulose which can be crosslinked with polyvalent ions, polyurethane hydrogel prepolymers and polymethylene isocyanates. A preferred prepolymer material is polyazetidine prepolymer. The polymer may be formed as a coating on a solid inert carrier.

11 Claims, No Drawings

IMMOBILIZED MICROBIAL CELL COMPOSITION FOR MAKING L-ASPARTIC ACID

The present invention is concerned with an improved process for manufacturing L-aspartic acid using immobilized microbial cells, notably *E. coli* (*Escherichia coli*) cells, which contain L-aspartase activity.

BACKGROUND TO THE INVENTION

There is a considerable amount of prior art regarding the immobilization of *E. coli* or other microbial cells for use in the preparation of L-aspartic acid. For example, U.S. Pat. No. 3,791,926 (Chibata et al) describes a process for the production of L-aspartic acid which involves polymerizing a monomer selected from acrylamide, N,N'-lower alkylene-bis(acrylamide) and bis(acrylamidomethyl) ether in an aqueous suspension containing an aspartase-producing microorganism such as *E. coli* ATCC No. 11303. The resultant immobilized aspartase-producing microorganism is treated with ammonium fumarate or a mixture of fumaric acid or its salt and an inorganic ammonium salt which by enzymatic reaction gives L-aspartic acid.

The immobilization of *E. coli* cells containing aspartase activity and use of the resulting immobilized cells for the production of L-aspartic acid are also described by Fusee et al, Applied and Environmental Microbiology, Vol. 42, No. 4, October 1981, pages 672–676. According to Fusee et al, the cells are immobilized by mixing a suspension of the cells with a liquid isocyanate-capped polyurethane prepolymer (Hypol®) so as to form a "foam" containing the immobilized cells.

Sato et al (Biochimica et Biophysica Acta, 570(1979) pages 179–186) have disclosed the immobilization of *E. coli* cells containing aspartase activity with κ-carrageenan, and use of the immobilized preparation for the production of L-aspartic acid.

Additional literature disclosures describing the immobilization of microbial cells in urethane prepolymers or polyurethanes or the like include the following:
(a) Immobilization of Microbial Cells in Polyurethane Matrices by Klein et al, Biotechnology Letters, Vol. 3, No. 2, 65–70 (1981);
(b) Hydrophilic Urethane Prepolymers: Convenient Materials for Enzyme Entrapment, Biotechnology & Bioengineering, Vol. XX, pages 1465–1469 (1978);
(c) Transformation of Steroids by Gel-Entrapped Cells in Organic Solvent by Omata et al, European J. Applied Microbiology and Biotechnology 8, 143–155 (1979); and
(d) Entrapment of Microbial Cells and Organelles With Hydrophilic Urethane Prepolymers, by Tanaka et al, European J. Applied Microbiology and Biotechnology, 7, 351–354 (1979).

The above-noted processes for preparing L-aspartic acid using immobilized microbial cells suffer from various disadvantages. For example, κ-carrageenan gum and polyurethane "foam" as disclosed by Fusee et al and Sato et al are relatively soft and compressible. Hence when these immobilized cell compositions are used, in a column through which ammonium fumarate is passed for conversion to ammonium aspartate, they tend to be compressed and plug up, particularly where high flow rates and/or relatively tall column heights are involved.

OBJECTS OF THE INVENTION

The principal object of the present invention is to provide an improved process for preparing L-aspartic acid using L-aspartase active microbial cells, preferably *E. coli* cells, which have been immobilized in a special way whereby the resulting composition is highly effective for the preparation of L-aspartic acid batchwise or in continuous fashion.

A more specific object includes the provision of an improved process for preparing L-aspartic acid from ammonium fumarate using immobilized *E. coli* cells which maintain optimum L-aspartase activity for relatively long periods of time. Another specific object of the invention is to provide novel immobilized microbial systems suitable for use in making L-aspartic acid which obviate problems encountered in prior procedures involving the use of immobilized cells. Other objects will also be hereinafter apparent.

SUMMARY OF THE INVENTION

According to one aspect of the invention, there is provided a process for preparing L-aspartic acid by contacting ammonium fumarate or its equivalent with an immobilized microbial cell composition comprising *E. coli* 11303 cells or equivalent cells containing L-aspartase activity, the cells being immobilized by means of a fixed, insoluble, crosslinked polymer obtained by curing a curable prepolymer material selected from the group consisting of polyazetidine prepolymers, carboxymethyl cellulose (CMC), polyurethane hydrogel prepolymers and polymethylene isocyanates cured at a temperature below the temperature at which the L-aspartase activity of the microbial cells is significantly reduced, the cell/crosslinked polymer composition constituting a coating on a solid inert carrier. The application of the immobilized cell/crosslinked polymer coating on the carrier provides a highly advantageous form of the cell/polymer composition for use in preparing L-aspartic acid. It is a particularly advantageous feature that the cell/polymer systems of the invention can be provided as a dry coating on the carrier without significant loss of the L-aspartase activity.

An especially preferred aspect of the invention contemplates the provision of immobilized *E. coli* cells having L-aspartase activity, the cells being immobilized by means of a crosslinked, water-insoluble polymer obtained by curing a polyazetidine prepolymer.

Broadly speaking, the invention is dependent on binding whole cells of *E. coli*, notably *E. coli* ATCC 11303, or the equivalent, which are known to have L-aspartase activity and therefore are capable of producing L-aspartic acid (or ammonium salt thereof) by conversion of ammonium fumarate, in a novel and useful configuration using a special crosslinked polymer system as set forth above to bind the cells.

The indicated prepolymer systems can be crosslinked at temperatures below 40° C. and in the presence of relatively large volumes of water containing *E. coli* cells without significantly deteriorating the L-aspartase activity of the cells. It is a surprising aspect of the invention that such aqueous crosslinking conditions leave the *E. coli* cells with their L-aspartase activity even though the cells are immobilized in insoluble, crosslinked polymer networks.

Another unique aspect of the invention is that the wet dispersion of the *E. coli* cells in the aqueous polymer solutions can be taken to dryness while the immobilized cells still surprisingly retain most of their original L-aspartase activity. The drying process has the advantage of providing strong, well-crosslinked, insoluble compositions in the form of coatings, membranes, particles, etc. having high concentrations of cells retaining L-aspartase activity.

The novel immobilized L-aspartase cell compositions disclosed herein have been found to outperform the immobilized L-aspartase active *E. coli* cell compositions previously reported by, for example, Fusee et al and Sata et al in the references noted above.

Prepolymer materials suitable for use to provide the crosslinked polymer network for immobilizing the *E. coli* cells according to the invention include:

(1) polyazetidine prepolymers which may be crosslinked in aqueous solution by reaction with >NH, —SH, —OH, —COOH; or other polyazetidines which may be crosslinked by H$_2$O removal, heat, or by changing to a more basic pH. The following is an idealized structure of a representative polyazetidine such as Polycup ®172 (Hercules, Inc.) which is useful for present purposes:

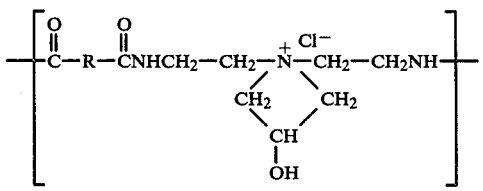

where R is typically —(CH$_2$)$_4$—

(2) carboxymethyl cellulose which can be crosslinked in aqueous solution by reaction with polyvalent ions such as Fe$^{+++}$, Al$^{+++}$, Ca$^{++}$, Mg$^{++}$. The following is an idealized structure of a carboxymethyl cellulose polymer such as CMC7HF (Hercules, Inc.):

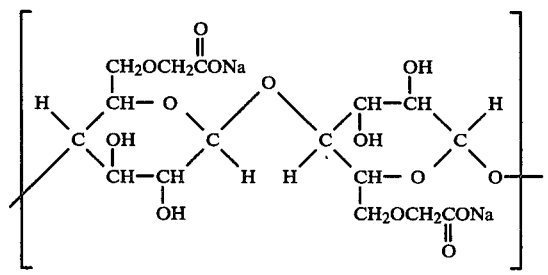

(3) polyurethane hydrogel prepolymers which can be crosslinked in aqueous solution by reaction with —NH, —SH, —OH, —COOH or H$_2$O. The following is an idealized structure of a representative polyurethane hydrogel prepolymer which is made by taking a water soluble polyether polyol having greater than two hydroxyl groups per molecule and a molecular weight greater than 3,000 and capping each hydroxyl group with a low molecular weight polyisocyanate:

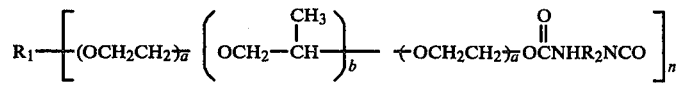

where $R_1$ typically is a low molecular weight polyol fragment (from glycerol, pentaerithritol, sorbitol, etc.);

a and b are integers, e.g. a and b are typically >10, generally 2 to 5, the sequence of arrangement of the a and b segments being random or in blocks;

n is also an integer typically >2; and $R_2$ is typically a diisocyanate such as a toluene diisocyanate, methylene di(phenylisocyanate), m-xylylene diisocyanate, isophorone-diisocyanate, hexamethylene diisocyanate, hexahydro-m-xylylene diisocyanate, dodecahydro-methylene di(phenylisocyanate) and the like; and (4) polymethylene isocyanates which can be cured by mixing with water such as the following:

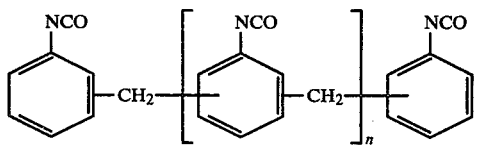

where n=0 to 4.

Such polyisocyanates are commercially available and are commonly called "crude polymeric methylene di(phenylisocyanates)". Other polyisocyanates which are convertible into crosslinked insoluble polymers with water are also thought to be useful, e.g. toluene diisocyanates, methylene di(phenylisocyanate), m-xylylene diisocyanate, isophoronediisocyanate, hexamethylene diisocyanate, hexahydro-m-xylylene diisocyanate, dodecahydro-methyl di(phenylisocyanate) and the like.

The isocyanates are usefully employed by coating an appropriate particulate substrate and then mixing with an aqueous slurry of *E. coli* cells.

Any of the above-noted polymer systems may be used to immobilize L-aspartase active *E. coli* cells to provide cell/polymer compositions having a variety of different forms and shapes. For example, the immobilized cell/polymer composition may be prepared in the form of membranes, filaments, fibers, tubes, beads or the like. A particularly important embodiment of the invention involves providing the immobilized cell/polymer composition as a coating on an appropriately shaped support which advantageously, although not necessarily, is in the form of solid or reticulated beads or particles composed of an inert solid organic or inorganic, porous or non-porous material. As noted earlier, the composition of the invention can be cured and dried without substantively affecting the L-aspartase activity of the cells and, as a consequence, the composition can be made up in the form of dried coated beads or other particulate material and stored until needed for use. Typically useful supports or carriers for the immobilized cell/crosslinked polymer compositions of the invention include the following in bead or particle form:

Molecular sieves
Ion exchange resins
Alumina
Silica and silica gel
Foraminifera skeletons Polymer latexes
Metals It is a useful property of the polymer systems used in the present invention that they can be contacted or mixed in water with *E. coli* cells containing L-aspartase and then crosslinked (or cured) to form insoluble and relatively fixed polymer matrices which hold or otherwise immobilize the *E. coli* cells. It is particularly useful that the crosslinking conditions which need to be used are mild enough so that the L-aspartase activity of the *E. coli* mutant cells is maintained.

As indicated, a particularly desirable composition according to the invention is obtained by applying the *E. coli* cells containing L-aspartase activity and the immobilizing polymer as a coating on hard inorganic or organic polymer beads. Using these relatively noncompressible compositions an L-aspartase active catalyst bed capable of high throughput in a fixed bed or fluidized bed is possible. As noted earlier, the L-aspartase active immobilized cell compositions previously described in the literature involving the use of relatively soft, compressible κ-carrageenan gum or polyurethane foam are compressible and therefore tend to plug under high flow rates, and/or tall column (bed) heights.

Various methods may be used to immobilize the *E. coli* ATCC 11303 cells, while retaining their L-aspartase activity, by combination with cured or crosslinked forms of prepolymers according to the invention. The preferred method used in any specific situation will depend, at least to some extent, on the prepolymer involved. Thus:

(a) In the case of the preferred polyazetidine prepolymers, *E. coli* ATCC 11303 cells are advantageously mixed with an aqueous solution of the prepolymer so as to obtain a homogeneous mixture after which the polyazetidine may be cured or crosslinked to give an insoluble L-aspartase active composition by any of the following means:

Removal of part or nearly all of the water at temperatures below 60° C. (usually between 40° and 0° C.) and pressures of 760 to 1.0 Torr; raising the pH above 7.5; exposing the *E. coli*/polyazetidine mixture to polyamines (using, for example, 100 parts of the composition for each 1-2 parts/wt. of polyethylene imine, polyamino ion exchange resins, diethylene triamine, ethylene diamine, etc.)

(b) For carboxymethyl cellulose (CMC) gums, homogeneous mixtures with *E. coli* ATCC 11303 may be crosslinked (cured) to insoluble, L-aspartase active coatings, membranes, fibers, beads, etc., by contacting an aqueous mixture of, for example, 1.0 part/wt. of cell paste/CMC mixture with an aqueous solution of 0.001 to 1.0 parts/wt. of polyvalent cation salt or, ideally 0.01 to 0.4 parts/wt. of polyvalent cation salt per 1.0 part/wt. of the cell paste/CMC mixture.

The resultant water insoluble immobilized cells/polymer network composition can be thus cured in the form of membranes, fibers or beads, but most efficiently as a coating around high surface area particles. As an illustration, 10 to 1000 parts/wt. of the high surface area particles may be coated with 1.0 part/wt. of cell paste/CMC mixture and ideally 50 to 500 parts/wt. of the particles per 1.0 part/wt. of cell paste/CMC mixture are used. Removal of 75% or more of the water contained in the cured coatings may be desirable to improve strength and bonding of the cell/polymer coating.

(c) When polyurethane hydrogels are used, homogeneous aqueous dispersions of *E. coli* ATCC 11303 (typically 1.0 g of cells per 1.0 to 1000 ml $H_2O$ broadly and 10 to 100 ml $H_2O$ preferably) are mixed with the hydrogel prepolymer and the prepolymer is cured into a water-insoluble L-aspartase active composition by allowing the polyisocyanate to react with water or in a more rapid manner by either removing 50 to 100% of the available water at 1000 to 0.1 Torr and below 50° C. (preferably 760 to 5.0 Torr and 0° to 30° C.) or by exposing the undried compositions to aqueous solutions of molecules having more than two primary or secondary amine groups. Typically these polyamine molecules can range from hydrazine or ethylene diamine to polyethylene imine. Generally for each 1.0 g of hydrogel prepolymer used, from 0.01 to 10.0 g of the polyamine in from 1.0 to 500 ml of water could be used. Ideally 0.1 to 1.0 g of the polyamine and 10 to 100 ml of water are employed per gram of hydrogel prepolymer used.

The above *E. coli*/hydrogel compositions can be fabricated into membranes, fibers, beads, etc.; but a preferred configuration is to use the compositions as coatings onto high surface area particles, as discussed before. Depending on the surface area of the particle employed from 0.1 to 100.0 g of the *E. coli*/hydrogel composition can be coated onto 100 g of the particle.

(d) In the case where polyisocyanates are used, these are generally first applied to a surface and the cells of *E. coli* ATCC 11303 thereafter added thereto. Usually, from 0.1 to 20.0 g of the polyisocyanate per 10.0 g of the surface material can be employed, preferably 0.5 to 10.0 g of polyisocyanate per 10.0 g of surface material. The polyisocyanates, if liquid, can be added undiluted to the substrate with good mixing (agitator or tumbling). However, the preferable method is to use solutions of the polyisocyanates in inert, readily evaporated solvents such as toluene, acetone, chloroform, tetrahydrofuran, dimethoxyethane, ethyl acetate, and the like. These solutions are added to the substrate, preferably dry particles of high surface area, with good mixing and the solvents removed at their boiling points at 760 Torr or below while continuing good mixing to insure homogeneously coated, mobile substrate particles. The amounts of solvents used will usually range from 1.0 to 100 parts/wt. per 1.0 parts/wt. of polyisocyanate.

The immobilized cell/polymer compositions of the invention may be used to make aspartic acid by either a batch or continuous process. However, it is noted that these compositions, particularly when coated onto a bead or other particulate support, are especially effective for the continuous conversion of aqueous solutions of ammonium fumarate to ammonium L-aspartate according to the following equation:

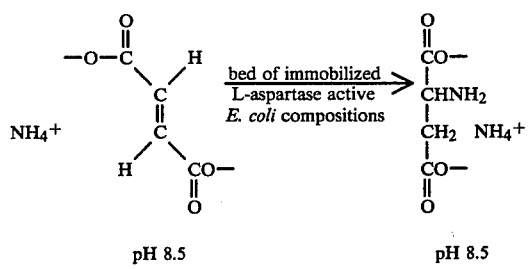

As illustrative of processes which may be used to prepare L-aspartic acid or ammonium L-aspartate according to the invention are the following:

(i) A batch type process wherein the catalyst compositions are stirred in from 0.1 to 5.0 molar (preferably 0.5 to 2.0 molar) solutions of ammonium fumarate in water at 5.0 to 10.0 pH (preferably 7.5 to 9.5 pH) for periods of 1.0 to 100 hours (preferably 8 to 48 hours) at temperatures below 50° C. (preferably 20° to 40° C.). Broadly from 0.05 to 50 g of immobilized cells, preferably from 1.0 to 15 g, are used per 1.0 mole of starting ammonium fumarate. After the conversion, the catalyst compositions may be removed by filtration or the equivalent for reuse in converting fresh batches of fumarate solutions. The product solutions are obtained in a form suitable for conventional processing to isolate the L-aspartic acid (acidification, precipitation, filtration, washing, recrystallization, drying).

(ii) A continuous process wherein the catalyst compositions, e.g. coated beads, are placed in columns and the solutions of ammonium fumarate (concentrations, pH's, and temperatures are the same as described above for the batch processes) are passed through the catalyst beds either from above or from below (fluidized bed mode). The rates of passage of these fumarate solutions may range from 0.1 to 1000 space velocities/hour. For example, 5.0 liters of solution per hour may be passed through 1.0 liter of catalyst bed representing 5.0 space velocities (S.V.) per hour. Preferably the fumarate solution flow rates which yield essentially 100% conversion of the fumarate to the L-asparate fall in the range of 0.5 to 20.0 S.V./hour. The effluent from these columns of catalyst beds is suitable for conventional processing to isolate L-aspartic acid (as outlined above in the batch processes).

The invention is illustrated by the following Examples:

EXAMPLE 1

Preparation of *E. coli* containing L-Aspartase Immobilized in CMC Gum

To 10 g of a 1% aqueous solution of high molecular weight carboxymethyl cellulose (Hercules 7 HF CMC gum, approximate molecular weight of 700,000 and 0.65 to 0.85 carboxymethyl groups per anhydroglucose units) was added 0.5 g of a paste of the *E. coli* cells, American Type Culture Collection #11303. A thoroughly homogeneous dispersion was made by hand mixing with a wooden stick. A 2.0 g aliquot of this dispersion was placed onto 10 g of hydrated 5A molecular sieve beads (8–12 mesh, previously hydrated by mixing 100 g of the beads with 200 g of water following by decanting the excess water and allowing the beads to dry at 25° C. in air). After a thorough mixing by hand for five to ten minutes, uniformly coated, damp, but free flowing, beads were obtained. These coated beads were then poured into 40 ml of a 0.1% solution of FeSO$_4$.n-H$_2$O in water. After 4 hours of periodic gentle stirring at 25° C. the liquid was decanted (considerable gel microparticles were noted in the liquid) and the beads washed four times with 0.1 M sodium phosphate buffer solution. A total of 22.2 g of wet coated beads were obtained. The beads were stored at 5° C. in damp air. For L-aspartase activity (see Table I) a 5.0 ml aliquot of these wet beads was taken. This aliquot weighed 6.3 g and was estimated to contain 0.027 g of the *E. coli* cells $$\left( \frac{0.5 \text{ g}}{10.5 \text{ g}} \times 2.0 \text{ g} \times \frac{6.3 \text{ g}}{22.2 \text{ g}} = 0.027 \text{ g} \right).$$

EXAMPLE 2

Preparation of *E. coli* cells containing L-Aspartase Immobilized In a Polyurethane Hydrogel (a) A polyurethane hydrogel prepolymer was prepared by capping a 7,000 molecular weight water soluble polyether (high level of polyoxyethylene segments) triol, Pluracol®V-7 from BASF Wyandotte, with three moles of dodecahydromethylene di(phenylisocyanate), Desmodur®W from Mobay Chemical Company. A solution of 1.0 g of this hydrogel prepolymer in 9.0 g of water was thoroughly mixed with 1.0 g of *E. coli* ATCC 11303 cell paste at 25° C. To 20 g of hydrated 5 Å 8–12 mesh molecular sieve beads was added a 2.0 g aliquot of the *E. coli*-hydrogel prepolymer aqueous dispersion. The resultant mixture was stirred over a period of 10 minutes by hand with a wooden stick at 25° C. to give 22.0 g of wet but free flowing coated beads. Preliminary experiments showed that 10% solutions of this hydrogel prepolymer in water formed water soluble gels upon drying at 25° C. in air for 8 to 24 hours. Thus, the wet coated beads were allowed to dry in the open air at 25° C. for 16 hours to give 20.1 g of free flowing cured coated beads. A 4.3 g aliquot of these coated beads had a volume of 5.0 ml and an estimated *E. coli* cell content of 0.039 g $$\left( \frac{1.0 \text{ g}}{11.0 \text{ g}} \times 2.0 \text{ g} \times \frac{4.3 \text{ g}}{20.1 \text{ g}} = 0.039 \text{ g} \right).$$

This 5.0 ml sample was used for L-aspartase activity measurements (see Table 1).

(b) A 1.0 g aliquot of the aqueous *E. coli*-hydrogel prepolymer dispersion described above was also coated onto 10.0 g of 5 Å, 8–12 mesh, hydrated molecular sieve beads at 25° C. After stirring for 5 to 10 minutes the resultant free flowing wet beads were poured with good mixing into 40 ml of a 0.1% solution of polyethylene imine (Aldrich Chemical Co. #18197-8) in water. Preliminary experiments showed that a fresh, less than 15 minute old, solution of 1.0 g of hydrogel prepolymer in 10 ml H$_2$O formed a water insoluble gel immediately upon contacting a 0.1% aqueous solution of the polyethylene imine. The slurry of coated beads in the polyethylene imine solution were gently stirred for 30 minutes at 25° C. and then washed four times with 40 ml portions of 0.1 M sodium phosphate buffer solution (pH 7.5) to give 11.5 g damp, free flowing beads. A 5.0 ml aliquot of those beads weighed 5.1 g and was estimated to contain 0.040 g of the *E. coli* cells $$\left( \frac{1.02 \text{ g}}{11.0 \text{ g}} \times 1.0 \text{ g} \times \frac{5.1 \text{ g}}{11.5 \text{ g}} = 0.041 \text{ g} \right).$$

This 5.0 ml aliquot was used for L-aspartase measurements (see Table I).

(c) A polyurethane hydrogel membrane having *E. coli* ATCC 11303 containing L-aspartase was prepared in the following manner:

A slurry of 10.0 g of *E. coli* ATCC 11303 cell paste in 10.0 g of phosphate buffered saline water (pH 7.4) was mixed for 30 minutes at 25° C. to insure a homogeneous dispersion. A solution of 5.0 g of the above mentioned hydrogel prepolymer (7,000 molecular weight triol capped with three moles of Desmodur ®W) in 10.0 g of deionized water was formed by vigorous stirring for one minute at 25° C. This solution was mixed with the homogeneous cell paste slurry. Within 20 seconds of vigorous stirring the resultant mixture became quite thick and was immediately poured onto a Teflon ® sheet. Within a few seconds at 25° C. the mixture became an elastomeric gel. After 45 minutes in air at 25° C. the resultant elastomeric membrane composite (1/16" to ¼" thick by 4" diameter) was stripped off the Teflon ® surface.

The membrane was placed in 500 ml of 1.5 M ammonium fumarate solution and shaken for 30 minutes. Considerable turbidity developed in the aqueous solution indicating cells and/or gel were washed out of the membrane. This washing process was repeated with one liter of the 1.5 M ammonium fumarate solution at 25° C. for 64 hours. The solution was only very slightly hazy and its optical density at 280 nm (1/1000 dilution) was 0.005 compared to 0.43 (1/1000 dilution) at the start. This indicates that essentially all the ammonium fumarate had been consumed.

The membrane was removed intact and placed in 750 ml fresh 1.5 M ammonium fumarate. After 16 hours of gentle stirring at 25° C. the clear product liquid over the membrane had an optical density at 280 nm (1/1000 dilution) of 0.005. This process was repeated with 750 ml more of the ammonium fumarate for 20 hours at 25° C. The combined 15,000 ml of product solution was clear and had an optical density at 280 nm of 0.005.

A 1000 ml aliquot of the combined product solution was acidified to a pH of 2.8 using 145 g of concentrated hydrochloric acid. The resultant slurry of white crystals was kept at 5° C. for 16 hours and then filtered. The damp filter cake was then stirred in 1000 ml of deionized water at 80° to 90° C. for 2 hours and then allowed to cool to 30° C. The white crystalline solids were collected by filtration and washed with 250 ml deionized water. The solids were dried at 25° C. to 100° C. and 5 to 20 Torr for 16 hours to a constant weight of 178.0 g which represents an 89.4% yield of L-aspartic acid $$\left( \frac{178.0}{1.5} \times 133 = 0.894 \right).$$

The optical rotation of a solution of 2.04 g of the white solid in 100 ml of 6.0 N HCl was measured on a Perkin-Elmer polarimeter at 25° C. and found to be +0.497. On the same instrument a solution of 2.04 g of an authentic sample of L-aspartic acid (Sigma Chemical Co. #A-9256) had a rotation of +0.495.

EXAMPLE 3

Preparation of *E. coli* Containing L-Aspartase Immobilized On Surfaces Pretreated with Polyisocyanates (a) A 10.0 g sample of activated anhydrous 5 Å, 8–12 mesh molecular sieve beads was mixed in a rotary evaporation apparatus with a solution of 2.0 g of a crude polymeric aromatic polyisocyanate (Upjohn Chemical Company PAPI ®20, 7.1 meg NCO/g) in 50.0 g of dry toluene. The toluene was removed at 85° C. and 10 to 20 Torr over a period of an hour of continued tumbling. The free flowing impregnated beads were cooled to 25° C. and a slurry of 1.0 g *E. coli* ATCC 11303 paste in 1.0 g of 0.1 M sodium phosphate buffer (pH 7.5) was added. The resultant bead mixture was tumbled slowly for four hours at 25° C. and one atmosphere to give 12.9 g dry free flowing beads. A 5.0 ml aliquot of the dry beads weighed 4.9 g. This volume did not change after soaking in 1.5 M ammonium fumarate solution. An estimated 0.38 g of *E. coli* cells were on this 5.0 ml aliquot $$\left( \frac{4.9 \text{ g}}{12.9 \text{ g}} \times 1.0 \text{ g} = 0.38 \text{ g} \right)$$

which was used to measure L-aspartase activity (see Table I).

(b) In a similar manner 10.0 g of anhydrous, weakly basic, >N—H form, ion exchange beads (Rohm & Haas, Amberlite ®IRA 45, 0.42 mm diameter dried at 85° to 90° C. and 5 to 20 Torr for several hours) were treated with a solution of 2.0 g PAPI ®20 in 50 ml dry toluene. Removal of the toluene at 85° to 90° C. and 5 to 20 Torr over a period of an hour gave a somewhat sticky but still mobile mass of coated beads. To this tumbled mixture was added a slurry of 1.0 g *E. coli* ATCC 11303 paste in 1.0 ml of 0.1 M sodium phosphate (pH 7.5) buffer solution. To aid in achieving a homogeneous coating of this rather gummy mass, sixty 0.25" diameter Teflon ® balls were added. The resultant mixture was tumbled at 25° C. and 5 to 20 Torr for two hours to give, after removal of the Teflon ® balls, 15.6 g of dry free flowing coated beads. A 5.0 ml aliquot of these coated beads weighed 2.8 g and did not change volume after soaking in 1.5 M ammonium fumarate solution. This 5.0 ml aliquot was used for L-aspartase measurements (see Table I) and was estimated to contain 0.18 g of *E. coli*

$$\left( \frac{1.0 \text{ g}}{15.6 \text{ g}} \times 2.8 \text{ g} = 0.18 \text{ g} \right).$$

EXAMPLE 4

Preparation of *E. coli* Containing L-Aspartase Immobilized With Polyazetidine Gels (a) A mixture of 2.0 g of an aqueous polyazetidine solution (Hercules Polycup ®172, as received 12% solids in H₂O) and 2.0 g of *E. coli* ATCC 11303 paste was stirred rapidly with a magnetic stirring bar for five minutes at 25° C., to insure a homogeneous dispersion. This mixture was then poured out onto a polystyrene surface to dry at 16 hours and 25° C. The resultant 2"×2"×1/16" thick flexible membrane was stripped from the surface and found to weigh 0.7 g. This film was used in L-aspartase measurements (see Table I) and was estimated to contain 2.0 g of *E. coli* cells (hydrated state).

(b) A homogeneous mixture of 2.0 g of Polycup ®172 and 2.0 g *E. coli* ATCC 11303 was distributed onto 30 g of hydrated 5 Å, 8–12 mesh molecular sieve beads by means of tumbling at 25° C. and 5 to 20 Torr for 45 minutes. After 16 more hours drying at 25° C. in open air the resultant coated beads weighed 30.4 g. A 5.0 ml aliquot of these coated beads weighed 3.9 g. This sample was used for L-aspartase activity (see Table I) and was estimated to have 0.26 g of *E. coli* cells $$\left(\frac{3.9 \text{ g}}{30.4 \text{ g}} \times 2.0 \text{ g} = 0.26 \text{ g}\right).$$

(c) A homogeneous dispersion of 2.0 g *E. coli* ATCC 11303 in 2.0 of Polycup®172 at 25° C. was dispersed onto 30.0 g of Amberlite®IRA 45 ion exchange beads (as received, 42% H$_2$O, >N—H form) by hand mixing with a wooden stick for 30 minutes at 25° C. A thin layer of the somewhat sticky mixture was allowed to stand in air at 25° C. for 16 hours. The resultant free flowing beads weighed 25.8 g. A 3.0 g sample of these dry coated beads had a volume of 5.0 ml. Upon soaking in 1.5 M ammonium fumarate solution the volume expanded to 5.5 ml. A 5.0 ml aliquot of these wet coated beads was taken for L-aspartase measurements (see Table I) and the estimated *E. coli* content was 0.21 g $$\left(\frac{3.0 \text{ g}}{25.8 \text{ g}} \times 2.0 \text{ g} \times \frac{5.0}{5.5} = 0.21 \text{ g}\right).$$

(d) A homogeneous dispersion of 2.0 g *E. coli* ATCC 11303 in 4.0 g deionized water and 2.0 g Polycup®172 was added over a period of 3.5 hours in three equal portions to 10.0 g of Amberlite®IRA 45 (as received, 42% H$_2$O, free >N—H form) containing sixty 0.25 diameter Teflon® balls. This mixture was tumbled at 25° C. at 5 to 20 Torr. After a total of five hours of drying at reduced pressure the resultant dry, coated beads (Teflon® balls removed) weighed 7.8 g. A 5.0 aliquot of these dry, free flowing coated beads weighed 2.9 g. After saturating with 1.5 M ammonium fumarate solution the volume swelled to 6.25 ml. A 5.0 ml aliquot of these wet, coated beads was taken for L-aspartase measurements (see Table I). The estimated *E. coli* content of this aliquot was $$\left(\frac{2.0 \text{ g}}{7.8 \text{ g}} \times 2.9 \text{ g} \times \frac{5.0}{6.25} = 0.59 \text{ g}\right).$$

(e) A homogeneous disperson of 3.0 g *E. coli* ATCC 11303 in 6.0 ml deionized water plus 3.0 g of Polycup®172 was spread onto 10.0 g of Amberlite®IRA 45 (as received, 42% H$_2$O, free >N—H form) in the same manner of drying at reduced pressure described above. A total of 10.7 g dry, coated, free flowing beads were obtained. A 5.0 ml aliquot of dry coated beads weighed 3.0 g. After soaking in 1.5 M ammonium fumarate solution this volume swelled to 5.75 ml. A 5.0 ml aliquot of the wet, coated beads was taken for L-aspartase measurement (see Table 1). The estimated *E. coli* content of this 5.0 ml aliquot was 0.73 g $$\left(\frac{3.0 \text{ g}}{10.7 \text{ g}} \times 3.0 \text{ g} \times \frac{5.0}{5.75} = 0.73 \text{ g}\right).$$

(f) A homogeneous dispersion of 4.0 g *E. coli* ATCC 11303 in 4.0 g of Polycup®172 and 8.0 g deionized water was added in approximately six equal portions over a 5.5 hour period at 25° C. and 5 to 20 Torr to 10.0 g of Amberlite®IRA 938 beads (Rohm and Haas, 73% H$_2$O, 0.38 mm diameter, tert. amine chloride salt form) containing eight 0.5" diameter Teflon® balls. After 6 hours total of tumbling at 25° C. and 5 to 20 Torr the resultant dry, coated free flowing beads weighed 10.3 g and had a volume of 16.6 ml. Soaking these beads in excess 1.5 M ammonium fumarate solution (pH 8.5) for 16 hours at 25° C. gave 17.5 ml wet beads. A 5.0 ml aliquot of the wet beads, estimated to contain 1.14 g *E. coli* ATCC 11303

$$\left(\frac{4.0 \text{ g}}{17.5 \text{ ml}} \times 5.0 \text{ ml} = 1.14 \text{ g}\right),$$

was taken for L-aspartase activity measurements (see Table I).

EXAMPLE 5

Coating Molecular Sieve Beads and Ion Exchange Resin Beads with *E. coli* Cells Containing L-Aspartase Using No Polymer Binders To demonstrate the utility of the above described polymer systems used to immobilize the *E. coli* cells containing L-aspartase, the following experiments were conducted to coat materials with the cells containing L-aspartase alone, i.e. with no polymer binders.

(a) A homogeneous slurry of 1.0 g *E. coli* cells, ATCC 11303, containing L-aspartase in 5.0 ml of Na phosphate buffer (0.1 M, pH 7.5) was added in four equal portions over a period of 3.5 hours to 10.0 g of hydrated 5 A molecular sieve beads (8-12 mesh) also containing ten 0.5" diameter Teflon® balls. This mixture was tumbled at 25° C. and 5 to 10 Torr. After a total of about 4.0 hours the resultant dry, coated, free flowing beads weighed 9.9 g. A 5.0 ml aliquot of these dry beads weighed 4.2 g. The volume did not change upon soaking in 1.5 M ammonium fumarate solution. The estimated *E. coli* cell content of this aliquot of coated beads was 0.42 g $$\left(\frac{1.02 \text{ g}}{9.9 \text{ g}} \times 4.2 = 0.42 \text{ g}\right).$$

A 5.0 ml aliquot of the coated beads was gently stirred in 50 ml 1.5 M ammonium fumarate solution at 25° C. for 24 hours. The solution became very turbid indicating considerable amounts of material were sloughing off the beads. The beads were isolated by decantation and again gently stirred in 50.0 ml fresh 1.5 M ammonium fumarate at 25° C. for L-aspartase activity measurement (see Table I). However, even after one hour the solution became very turbid again. On several more occasions the beads were isolated and gently stirred in fresh 1.5 M ammonium fumarate solution. The beads continued to give off considerable amounts of material to make the solutions very turbid. This behavior was not observed in any of the preparations of L-aspartase active cell coatings of beads where the polymer binders were also added to the formulation. In all the polymer binder examples the ammonium fumarate solutions over the coated beads remained clear.

(b) In a similar way, a slurry of 10.0 g *E. coli* ATCC 11303 in 30 g of aqueous phosphate buffer solution (0.1 M, pH 7.5), but no polymer binders, was coated onto 50.0 g of Amberlite®IRA 45 (as received from Rohm and Haas, 42% H$_2$O, >N—H form) over a period of 4.5 hours at 25° C. and 5 to 20 Torr. The resultant 47.6 g of free flowing dry, coated beads had a volume of 83.5 ml. Upon soaking these beads in excess 1.5 M aqueous ammonium fumarate the solution became thick and opaque from the massive amount of material detached from the beads. All attempts to filter (cotton wadding, fiberglass mat, 43 mesh nylon screen, medium porosity sintered glass) off the beads from this opaque mother liquid failed because the thick gelatinous particles quickly plugged the filters. This behavior was not observed in any of the examples where the polymer binders were incorporated into the formulation. In these cases the aqueous solutions over the beads remained clear at all times, and flowed quickly through filters.

EXAMPLE 6

L-Aspartase Activity Measurements

Shown in Table I are the L-aspartase activities of the immobilized *E. coli* ATCC 11303 compositions described in the preceding examples. In each case the samples were preconditioned by gently shaking in 50 ml of a 1.5 M ammonium fumarate solution in deionized water (pH 8.5) containing 0.002 M $MgSO_4$ for a period of 8 to 16 hours at 25° C. The solution was then drained from each sample and 50 ml fresh fumarate solution added prior to gentle shaking again for 8 to 16 hours at 25° C. At this point all the samples prepared with the polymer binders discussed in the previous examples showed no evidence of material sloughing off the solid supports; i.e., their supernatent solutions were all clear. Samples prepared using no polymer binders (Example 5) continued to give very turbid supernatant solutions even after several washings. This indicates the cell material was not securely bound to the solid supports.

The next step in each example was to take a 5.0 ml aliquot (or in the case of the membrane, a 2"×2"×0.125" section) of the washed and well drained composites and gently shake in a fresh 50.0 ml of the above mentioned ammonium fumarate solution at 25° C. Samples were removed after 60 minutes and diluted 1/1000 with deionized water. The decrease in optical density at 280 nm from the starting 1.5 M ammonium fumarate solution (observed to be 0.43 at 1/1000 dilution) indicated the L-aspartase activity. The optical density of a 1.5 M L-aspartic acid ammonium salt (pH 8.5) at 280 nm is essentially zero (<0.005).

The observed conversion of the fumarate to the L-aspartate is shown in Table I as moles of aspartic acid/hr/liter of catalyst bed and as moles of aspartic acid/hr/kg wet *E. coli*. For example in experiment 4d using polyazetidines, cell paste and ion exchange beads, the optical density at 280 nm dropped from 0.43 to 0.32 after 60 minutes at 25° C. The calculations are:

$$\frac{0.43-0.32}{0.43} \times 1.5 \text{ moles} \times \frac{50 \text{ ml}}{1000 \text{ ml}} \times \frac{1000 \text{ ml}}{5.0 \text{ ml}} =$$

3.8 moles ASP/hr/l catalyst bed $$\frac{0.43-0.32}{0.43} \times 1.5 \text{ moles} \times \frac{1000 \text{ g/kg}}{0.59 \text{ g wet cells}} \times \frac{50 \text{ ml}}{1000 \text{ ml}} =$$

32.5 moles ASP/hr/kg wet cells

Also shown in Table I are values calculated from data in the literature showing the L-aspartase performance at 37° C. of a polyurethane foam (HYPOL ®) containing *E. coli* ATCC 11303. Here a 0.777 l bed having 126 g of cells required 32 minutes to convert 2.0 liters of 1.0 M fumarate 100% to L-aspartate at 37° C. These workers also report the average rate of conversion of 1.5 M fumarate to be 8% lower than 1.0 M fumarate solution. They also observed rates of 37° C. to be 1.67 times rates at 25° C. Thus a fair estimate of their L-aspartic acid production rate for comparison to our data (25° C., 1.5 M fumarate) is:

$$\frac{2.0 \text{ l}}{\frac{32}{60} \text{ hrs} \times 0.77 \text{ l bed}} \times 1.0 \text{ moles/l} \times 0.92 \times \frac{1}{1.67} =$$

$$\frac{2.69 \text{ moles L-ASP}}{\text{hr} \times \text{l cat. bed}}$$

$$\frac{2.0 \text{ l}}{0.126 \text{ kg cell} \times \frac{32}{60} \text{ hrs}} \times 1.0 \text{ moles/l} \times 0.92 \times \frac{1}{1.67} =$$

$$\frac{16.4 \text{ moles L-ASP}}{\text{hr} \times \text{kg cells}}$$

Comparing these values to the data obtained representative of the present invention shows the superiority of the present process over the polyurethane foam system.

TABLE I

| | ASPARTASE ACTIVITY OF BOUND *E. COLI* (ATCC 11303) AT 25° C. | | | |
|---|---|---|---|---|
| EXAMPLE # | BINDING METHOD | Moles of ASP (hr × l cat. bed) | Moles of ASP (hr × kg wet *E. coli*) | Est. g of *E. coli* used (per 5.0 ml bed samp) |
| 1 | CMC + $Fe^{+++}$ on M.S. beads | 0.87 | 185 | 0.027 |
| 2a | P.U. Hydrogel via drying on M.S. beads | 0.45 | 57.7 | 0.039 |
| 2b | P.U. Hydrogel via poly EI on M.S. beads | 0.27 | 33.8 | 0.040 |
| 3a | PAPI 20 on M.S. beads | 2.5 | 32.9 | 0.38 |
| 3b | PAPI 20 on I.E. beads | 1.2 | 33.3 | 0.18 |
| 4a | Polycup 172 film | | 65.0 | 0.80 |
| 4b | Polycup 172 on M.S. beads | 0.6 | 11.5 | 0.26 |
| 4c | Polycup 172 on I.E. beads | 1.0 | 23.8 | 0.21 |
| 4d | Polycup 172 on I.E. beads | 3.8 | 32.5 | 0.59 |
| 4e | Polycup 172 on I.E. beads | 3.9 | 26.7 | 0.73 |
| 4f | Polycup 172 on I.G. beads | 12.75 | 55.9 | 1.14 |
| 5a | *E. coli* alone (No binder) on M.S. beads | 2.6* | 30.9* | 0.42* |
| — | HYPOL foam (estimate from data of Fusee et. al)[2] | 2.69 | 16.4 | |

*Massive amounts of cells sloughed off the beads, thus much of the activity shown is caused by unbound cells.

EXAMPLE 7

Continuous Production of L-Aspartic Acid

A 5.0 ml aliquot of the wet beads from Example 4d were placed in a 0.7 cm diameter×15 cm jacketed glass column. The column temperature was maintained at 37° C. A fresh 1.5 M ammonium fumarate solution in deionized water containing 0.002 m MgSO$_4$ (all at pH 8.5) was continuously passed up through the bed of beads at a rate of 0.5 ml/min. Samples of the effluent product solution were taken periodically and analyzed for L-aspartate content as 1/1000 dilutions in deionized water as described in Example 6. The bulk of the effluent was collected but not returned to the column. The following data show that over a period of 50 days of continuous running the L-aspartase activity of the coated beads remained essentially unchanged.

| Time, days | L-aspartate content of effluent, % |
|---|---|
| 1 | 59.6 ⎫ |
| 25 | 61.5 ⎬ 62.5 average |
| 50 | 66.5 ⎭ |

At the 62.5% conversion rate for a flow of 6.0 bed volumes/hr (0.5 ml/min through 5.0 ml of catalyst bed) the production rate of L-aspartic acid is:

$$\frac{6.0 \text{ l}}{\text{hr} \times \text{l cat bed}} \times 0.625 \times \frac{1.5 \text{ moles}}{1} = \frac{5.6 \text{ moles L-ASP}}{\text{hr} \times \text{l cat bed}}$$

For a period of one hour at 37° C. the same column was run at the rate of 4.0 bed volumes/hr (0.33 ml/min through 5.0 ml of catalyst bed) and the average rate of fumarate (1.5 M) conversion was 80.0%. This corresponds to:

$$\frac{80.0}{62.5} \times 5.6 = \frac{7.2 \text{ moles L-ASP}}{\text{hr} \times \text{l cat bed}}$$

Based on these conversion rates of 62.5% and 80.0% at 6.0 and 4.0 bed vol/hr respectively, a conservative estimate by graphical methods, of the flow rate required to achieve 100% conversion is $$\frac{1.5 \text{ bed volumes}}{\text{hr}}.$$

At 1.5 bed volumes/hr the L-ASP production rate is:

$$\frac{1.5 \text{ l}}{\text{hr} \times \text{l bed}} \times \frac{1.5 \text{ moles L-ASP}}{1} = \frac{2.25 \text{ moles L-ASP}}{\text{hr} \times \text{l cat bed}}$$

These values (100% conversion at 1.5 bed vol/hr, and $$\frac{2.25 \text{ moles L-ASP}}{\text{hr} \times \text{l cat bed}}$$

are significantly better than the values of 1.1 bed vol/hr for 100% conversion and $$\frac{1.65 \text{ moles L-ASP}}{\text{hr} \times \text{l cat bed}}$$

reported for the continuous operation of a column of *E. coli* ATCC 11303 cells immobilized on κ-carrageenan gel.

It will be appreciated that various modifications may be made without deviating from the invention, the scope of which is defined in the following claims wherein:

We claim:

1. A process for preparing L-aspartic acid which comprises contacting ammonium fumarate with an immobilized microbial cell composition comprising cells containing L-aspartase activity immobilized by means of an insoluble, crosslinked polymer obtained by curing a curable polyazetidine prepolymer, said prepolymer being cured at a temperature below the temperature at which the L-aspartase activity of the microbial cells is significantly reduced, the cell/crosslinked polymer composition constituting a coating on a solid inert carrier.

2. A process according to claim 1 wherein the cells are whole cells of *E. coli* ATCC 11303.

3. A process according to claim 2 wherein the carrier comprises beads or other particulate material.

4. A composition comprising immobilized *E. coli* cells having L-aspartase activity, the cells being immobilized by means of an insoluble, crosslinked polymer obtained by curing a curable polyazetidine prepolymer, said prepolymer being cured at a temperature below the temperature at which the L-aspartase activity of the microbial cells is significantly reduced, the cell/crosslinked polymer composition constituting a coating on a solid inert carrier.

5. A composition according to claim 4 wherein the carrier is a particulate support.

6. A process for preparing an immobilized microbial cell composition which comprises mixing together an aqueous dispersion of cells containing L-aspartase activity and a polyazetidine prepolymer which is capable of being cured into a crosslinked polymer and curing the polyazetidine prepolymer in said mixture at a temperature below the temperature at which the L-aspartase activity of the cells is significantly reduced, the cells being thereby immobilized by the cured polyazetidine polymer.

7. A composition obtained by the process of claim 6 comprising cells having L-aspartase activity immobilized by said cured, crosslinked polyazetidine polymer.

8. A composition according to claim 7 wherein the cells are *E. coli* cells.

9. A composition according to claim 7 and comprising a coating of the immobilized cells on a particulate support.

10. The process of claim 6 wherein the polazetidine prepolymer in the mixture is cured after application of the mixture as a coating to a carrier.

11. The process of claim 10 wherein the coating is dried.

* * * * *

UNITED STATES PATENT AND TRADEMARK OFFICE
CERTIFICATE OF CORRECTION

PATENT NO. : 4,436,813

DATED : March 13, 1984

INVENTOR(S) : Louis L. Wood and Gary J. Calton

It is certified that error appears in the above-identified patent and that said Letters Patent is hereby corrected as shown below: On the title page;

[56] References Cited

Patentee for 4,237,229 should be --Hartdegen et al--
Fusee publication, correct spelling of --Escherichia--
Hustad publication, correct spelling of --Galactosidase-- and change (pp. 1111-1177) to --pp.1111-1117--

Column 3, line 11, correct spelling of --Sato--

Column 4, line 30, insert a hyphen between "isophorone-diisocyanate"

Column 9, after line 46, should read $--\left(\frac{178.0}{1.5 \times 133} = 0.894\right)--$ line 67, correct spelling of "meq"

Column 11, line 30, after "sixty" should read --0.25"--

Column 12, line 39 and the next line, "0.42 g" should be --0.43 g--

UNITED STATES PATENT AND TRADEMARK OFFICE
CERTIFICATE OF CORRECTION

PATENT NO. : 4,436,813

DATED : March 13, 1984

INVENTOR(S) : Louis L. Wood and Gary J. Calton

It is certified that error appears in the above-identified patent and that said Letters Patent is hereby corrected as shown below:

Columns 13-14, last line of Table I, after "Fusee et al)" delete the footnote "2"

Column 15, line 9, after "0.002" change "m" to --M--

Signed and Sealed this

Twenty-fourth Day of September 1985

[SEAL]

Attest:

Attesting Officer

DONALD J. QUIGG

Commissioner of Patents and Trademarks—Designate